US012622849B2

(12) United States Patent
Jang et al.

(10) Patent No.: US 12,622,849 B2
(45) Date of Patent: May 12, 2026

(54) COLORATION COSMETIC COMPOSITION WITH VARIABLE-COLOR CAPSULES

(71) Applicant: KOLMAR KOREA CO., LTD., Sejong (KR)

(72) Inventors: Sun Haeng Jang, Seoul (KR); Sang Keun Han, Cheonan (KR)

(73) Assignee: KOLMAR KOREA CO., LTD., Sejong (KR)

( * ) Notice: Subject to any disclaimer, the term of this patent is extended or adjusted under 35 U.S.C. 154(b) by 874 days.

(21) Appl. No.: 17/427,888

(22) PCT Filed: Jun. 21, 2019

(86) PCT No.: PCT/KR2019/007516
§ 371 (c)(1),
(2) Date: Aug. 2, 2021

(87) PCT Pub. No.: WO2020/184784
PCT Pub. Date: Sep. 17, 2020

(65) Prior Publication Data
US 2022/0117862 A1 Apr. 21, 2022

(30) Foreign Application Priority Data

Mar. 13, 2019 (KR) ........................ 10-2019-0028912

(51) Int. Cl.
| *A61K 8/11* | (2006.01) |
| *A61K 8/34* | (2006.01) |
| *A61K 8/65* | (2006.01) |
| *A61K 8/73* | (2006.01) |
| *A61K 8/9789* | (2017.01) |
| *A61Q 19/02* | (2006.01) |
| *A61Q 19/08* | (2006.01) |

(52) U.S. Cl.
CPC ................. *A61K 8/11* (2013.01); *A61K 8/34* (2013.01); *A61K 8/65* (2013.01); *A61K 8/73* (2013.01); *A61K 8/9789* (2017.08); *A61Q 19/02* (2013.01); *A61Q 19/08* (2013.01); *A61K 2800/42* (2013.01); *A61K 2800/882* (2013.01)

(58) Field of Classification Search
CPC ....... A61Q 19/00; A61Q 19/007; A61Q 19/08
See application file for complete search history.

(56) References Cited

U.S. PATENT DOCUMENTS 5,089,269 A * 2/1992 Noda ........................ A61K 8/11
424/59
2011/0165208 A1 7/2011 Kim et al.

FOREIGN PATENT DOCUMENTS

| CN | 104168873 A | 11/2014 |
| KR | 10-0347665 B1 | 8/2002 |
| KR | 10-2014-0113729 A | 9/2014 |
| KR | 10-2015-0042440 A | 4/2015 |
| KR | 20200029855 A | 3/2020 |
| WO | 2011/027960 A2 | 3/2011 |

OTHER PUBLICATIONS

Anonymous, Monthly ingredient feature—Guaiazulene, Oct. 5, 2016, 4 pages (Year: 2016).*
Fiori, J. et al., Study on the photostability of guaiazulene by high-performance liquid chromatography/mass spectrometry and gas chromatography/mass spectrometry, 2008, Rapid Communications in Mass Spectrometry, vol. 22, 2698-2706 (Year: 2008).*
International Search Report and Written Opinion for PCT/KR2019/007516 dated Dec. 6, 2019; 9 pages, including English translation.

* cited by examiner

*Primary Examiner* — Bethany P Barham
*Assistant Examiner* — Paul Hoerner
(74) *Attorney, Agent, or Firm* — Bridgeway IP Law Group, PLLC; Sang Ho Lee; Hyun Woo Shin

(57) ABSTRACT

The present invention relates to a capsule coloration cosmetic composition in which, when in use, the color of capsules is changed. The present invention provides a capsule coloration cosmetic composition comprising: a first formulation comprising capsules; and a second formulation comprising a colored oil-soluble ingredient, wherein the outer membranes of the capsules comprise a mixed gum comprising: acacia gum; and at least one of gelatin and agar, and wherein an oil-based emollient is included inside the capsules.

5 Claims, 3 Drawing Sheets

Blue     Yellow     Orange     Green     Red (a)       (b)        (c)        (d)       (e)

COLORATION COSMETIC COMPOSITION WITH VARIABLE-COLOR CAPSULES

CROSS REFERENCE TO RELATED APPLICATIONS

The present application is a national phase entry under 35 U.S.C. § 371 of International Application No. PCT/KR2019/007516, filed Jun. 21, 2019 which designates the United States of America, which claims priority to KR Application No. 10-2019-0028912, filed Mar. 13, 2019, the entire disclosures of each of these applications are hereby incorporated by reference in their entireties and for all purposes.

TECHNICAL FIELD

The present invention relates to a capsule coloration cosmetic composition in which the color of capsules is changed by mixing two formulations in use.

BACKGROUND ART

Recently, in cosmetic products, for the purpose of enhancing aesthetic effects, a method of differentiating the appearance by using colored capsules has been used.

However, there was a limit to implementing a capsule composition that is changed in color when applied to a formulation, and until now, by including a colorant inside capsules, only a cosmetic composition that changes the color of the capsules only after breaking the capsules is disclosed.

Meanwhile, with the development of dermatology, as gradually shifting to emphasizing the effects on the skin such as skin whitening, anti-aging, and alleviating acne. As the trend is gradually shifted toward emphasizing the effects on the skin, such as skin whitening, anti-aging, and acne relief, the concept of functional cosmetics (cosmeceuticals) emerged as an extension of the concept of cosmetics. However, most of the aforementioned functional ingredients are chemically unstable and there are many substances that are liable to deteriorate by moisture, light, heat, oxygen, etc. Thus, in order to apply the functional ingredients to cosmetics, there is a need for a technology for stabilizing the functional ingredients so as to maintain the original activities thereof without being altered in the manufacturing and distribution process.

Accordingly, it is necessary to develop a cosmetic composition that can give an aesthetic effect while enhancing the long-term stability of functional ingredients.

PRIOR ART DOCUMENT

Patent Literature: KR 10-0347665 B1

DESCRIPTION OF EMBODIMENTS

Technical Problem

It is an object of the present invention to provide a capsule coloration cosmetic composition that can give an aesthetic feeling by changing the color of capsules while having high long-term stability.

Solution to Problem

To achieve the object of the present invention, the present invention provides a capsule coloration cosmetic composition comprising: a first formulation comprising capsules;

and a second formulation comprising a colored oil-soluble ingredient, wherein the outer membranes of the capsules comprise: a mixed gum comprising acacia gum; and at least one of gelatin and agar, and an oil-based emollient is included inside the capsules.

According to an embodiment of the present invention, the first formulation and the second formulation are included in a weight ratio of 1:0.01 to 1:0.3.

According to an embodiment of the present invention, the capsules are included in an amount of 0.01 to 50 wt %, based on the total weight of the composition of the first formulation.

According to an embodiment of the present invention, the first formulation contains water in an amount of 40 to 90 wt %.

According to an embodiment of the present invention, the mixed gum is included in an amount of 1 to 10 wt %, based on the total weight of the composition of the capsule.

According to an embodiment of the present invention, in the mixed gum, the acacia gum and the other gums are mixed in a weight ratio of 1:0.01 to 1:1.

According to an embodiment of the present invention, the oil-based emollient is included in an amount of 10 to 90 wt %, based on the total weight of the composition of the capsules.

According to an embodiment of the present invention, in the capsule composition, water is included in an amount of less than 10 wt %, based on the total weight of the composition of the capsules.

According to an embodiment of the present invention, the first formulation further includes a polyol, and the capsules and the polyol are mixed in a weight ratio of 1:1 to 1:3.

According to an embodiment of the present invention, the oil-soluble ingredient is included in an amount of 0.001 to 5.0 wt %, based on the total weight of the composition of the second formulation.

According to an embodiment of the present invention, water is not included in the second formulation.

Advantageous Effects of Disclosure

In the capsule coloration cosmetic composition according to the present invention, when a user mixes a first formulation comprising capsules and a second formulation comprising an oil-soluble ingredient immediately before use, the oil-soluble ingredient is absorbed into the capsules and the color of the capsules is changed, and thus the user can directly visually identify that the oil-soluble ingredient enters the capsules, thereby increasing the reliability of the cosmetic composition.

In addition, during a distribution process from manufacture and sale until reaching consumers and even immediately before use by the user, the capsule coloration cosmetic composition according to the present invention is distributed in a state in which the oil-soluble ingredient is included in the second formulation without water while being separated from the first formulation containing water, thereby increasing the long-term stability of the oil-soluble ingredient.

In addition, even if the oil-soluble ingredient is mixed in the first formulation containing a large amount of water as the user mixes the first formulation with the second formulation, the oil-soluble ingredient is absorbed into the capsule contained in the first formulation to thus be re-protected, thereby additionally enhancing the long-term stability.

In addition, since the user is aesthetically affected by the long-term stability and reliability of the oil-soluble ingredient as well as the appearance of the color change when in use, consumption desire can be increased.

In addition, by including an oil-soluble pigment having a function as an oil-soluble ingredient, or by adding a pigment along with a specific function, the function of the cosmetic composition can be expressed only by color, thereby allowing even the elderly with presbyopia to easily distinguish functional cosmetics.

BEST MODE

Figure 1:
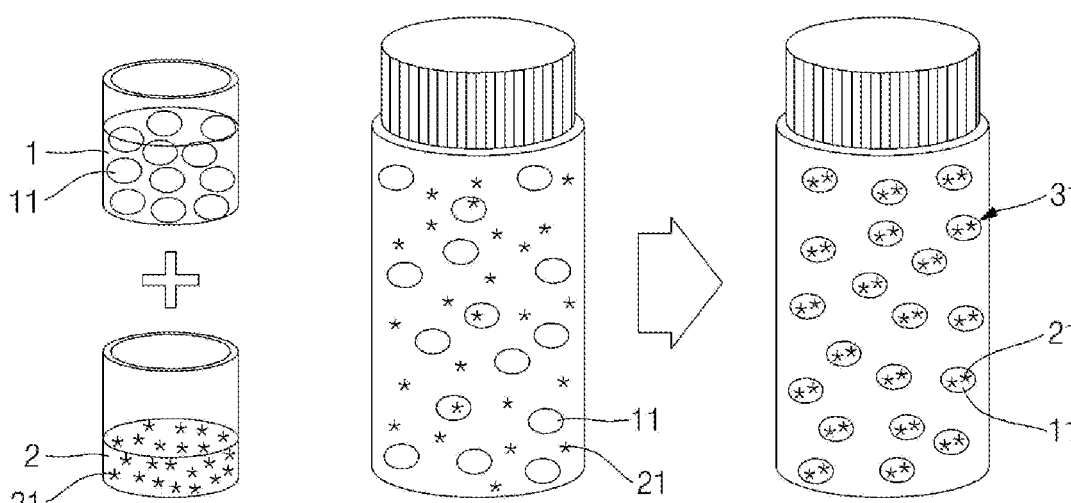
FIG. 1 is a diagram schematically showing a change in the color of capsules when an oil-soluble ingredient is absorbed into the capsules by mixing a first formulation comprising transparent capsules and a second formulation, prepared according to an embodiment of the present invention.

Hereinafter, the present invention will be described in more detail, which is, however, is for the purpose of explanation of the present invention and should not be construed as limiting the scope of the present invention.

According to an embodiment of the present invention, the present invention provides a capsule coloration cosmetic composition comprising: a first formulation comprising capsules; and a second formulation comprising a colored oil-soluble ingredient, wherein the outer membranes of the capsules comprise a mixed gum comprising: acacia gum; and at least one of gelatin and agar, and wherein an oil-based emollient is included inside the capsules. It is preferable that water is not included inside the capsules.

The term "capsule" used herein includes an outer membrane prepared by mixing gelatin, agar, gellan gum, cellulose gum, Arabic gum, collagen, etc. based on acacia gum, and contains an oil-based emollient therein.

According to an embodiment of the present invention, the mixed gum preferably includes acacia gum and gelatin, or acacia gum and agar. If the mixed gum is composed of only gums other than acacia gum, the absorption rate of the oil-soluble ingredient may decrease.

According to an embodiment of the present invention, the capsules may include a transparent formulation. According to another embodiment of the present invention, the capsule may be prepared as a colored capsule including a pigment. The pigment may be any pigment used in the art, and preferably a natural pigment or an oil-soluble pigment may be used.

According to an embodiment of the present invention, the first formulation and the second formulation are included in a weight ratio of 1:0.01 to 1:0.3, preferably 1:0.02 to 1:0.2, and most preferably 1:0.05 to 1:0.1. If the content of the second formulation is lower than the weight ratio of 1:0.01, the function of the oil-soluble ingredient cannot be properly exhibited and the color change is not noticeable. If the content of the second formulation exceeds the weight ratio of 1:0.3, the long-term stability is lowered, and the discoloration may be accelerated.

According to an embodiment of the present invention, the capsules are included in an amount of 0.01 to 50 wt %, preferably 1 to 30 wt %, and most preferably 2 to 8 wt %, based on the total weight of the composition of the first formulation. If the amount of the capsule included is less than 0.01 wt %, the capsule coloration effect and the long-term stability effect of the oil-soluble ingredient may be lowered, and if the amount of the capsule included is more than 50 wt %, the feeling of use of the cosmetic composition may be lowered due to an increase in oily feeling.

According to an embodiment of the present invention, the mixed gum is included in an amount of 1 to 10 wt %, preferably 2 to 8 wt %, and most preferably 3 to 5 wt %, based on the total weight of the composition of the capsules. If the amount of the mixed gum is less than 1 wt %, it may be difficult to maintain the shape of the capsules for a long period of time, and if the amount of the mixed gum exceeds 10 wt %, the feeling of use of the cosmetic composition may be deteriorated due to deterioration of capsule brittleness.

According to an embodiment of the present invention, the acacia gum is included in an amount of 0.1 to 7.0 wt %, preferably 1.0 to 5.0 wt %, more preferably 2 to 4 wt %, based on the total weight of the composition of the capsules. If the amount of the acacia gum is less than 0.1 wt %, the capsule may not be formed, and if the amount of the acacia gum exceeds 7.0 wt %, the brittleness of the capsule may be poor.

In the mixed gum, the acacia gum and the other gums are mixed in a weight ratio of 1:0.01 to 1:1, preferably 1:0.02 to 1:0.7, and most preferably 1:0.05 to 1:0.5. If the acacia gum is included in a weight ratio of less than 1:0.01, the absorption rate of the active ingredient is reduced, and when it is included in a weight ratio of 1:1, it may be difficult to use as a cosmetic composition due to poor brittleness.

According to an embodiment of the present invention, the oil-based emollient is included in an amount of 10 to 90 wt %, preferably 50 to 85 wt %, more preferably 70 to 80 wt %, based on the total weight of the composition of the capsules. If the amount of the oil-based emollient is less than 10 wt %, the absorption rate of the oil-soluble ingredient may be lowered, and if the amount of the oil-based emollient exceeds 90 wt %, the shape retention rate of the capsule may fall.

According to an embodiment of the present invention, in the capsule composition, water is preferably included in an amount of less than 10 wt %. When the amount of water included in the capsules exceeds 10 wt %, the long-term stability of the oil-soluble ingredient, which is affected by the functionality by water, may be lowered. However, in the case of an oil-soluble ingredient that is not significantly affected by water, the amount of water may be appropriately adjusted by a person skilled in the art.

According to an embodiment of the present invention, in the first formulation, the capsules and the polyol are mixed in a weight ratio of 1:1 to 1:3. When the polyol is contained in a weight ratio of less than 1:1 relative to the capsules, a difference in the transparency of the formulation may occur, and when the polyol is contained in a weight ratio of greater than 1:3, the feeling of use may decrease.

According to an embodiment of the present invention, the oil-soluble ingredient is included in an amount of 0.001 to 5.0 wt %, preferably 0.001 to 3.0 wt %, more preferably 0.01 to 0.2 wt %, based on the total weight of the composition of the second formulation.

According to an embodiment of the present invention, the second formulation does not include water. When water is included in the second formulation, the long-term stability of the oil-soluble ingredient, which may have poor functionality, may be reduced by contact with water, and the inflowability of the oil-soluble ingredient into the capsules may be reduced.

According to an embodiment of the present invention, useful examples of the oil-based emollient may include one or more selected from the group consisting of ethylhexystearate, isopropyl myristate, ethyl laurate, ethyl myristate, isopropyl palmitate, triglyceride, diglyceride, monoglyceride, diglyceride, glyceryl trioctanoate, octadodecyl myristate, isostearyl isostearate, dicapryl carbonate, isopropyl palmitate, octyl palmitate, caprylic/capric triglyceride, butylene glycol dicaprylate/dicaprate, triethylhexa senile, cetylethylhexanoate, isopropyl myristate, octyldodecanol, liquid paraffin, petrolatum, hydrogenated polydecene, squalene, cyclomethicone, phenyltrimethicone, cyclopentasiloxane, and dimethicone, and preferably, caprylic/capric triglyceride, hydrogenated polydecene, squalene, dimethicone, etc. may be used.

According to an embodiment of the present invention, the capsules may further include a moisturizer, and the moisturizer is any one or more selected from the group consisting of amino acid, diglycerin, erythritol, glycerin, glycerol polymer, hyaluronic acid, inositol, lactitol, maltitol, maltose, mannitol, natural moisturizing factor, polyglyceryl sorbitol, methylpropanediol, butylene glycol, 1,2-hexanediol, 1,3-propanediol, sorbitol, collagen, and agar, and glycerin, methyl propanediol, butylene glycol, 1,2-hexanediol, 1,3-propanediol, etc. is preferably used.

According to an embodiment of the present invention, at least one of the first formulation and the second formulation may further comprise a polyol, and the polyol compound may be selected from the group consisting of glycerin, erythritol, xylitol, maltitol, butylene glycol, propylene glycol, dipropylene glycol, sorbitol, 1,3-propane diol, hexylene glycol, polyethylene glycol, methylpropanediol, and combinations thereof, and preferably, glycerin, 1,3-propanediol, methylpropanediol, and the like may be used.

According to an embodiment of the present invention, the first formulation may further comprise a thickener, and the thickener may be xanthan gum, gellan gum, carbomer, sodium polyacrylate, and one or more selected from the group consisting of acrylate/C10-30 alkyl acrylate crosspolymer, sodium polyacrylate, ammonium acryloyl dimethyl taurate/VP copolymer, polyacrylate cross polymer, and sodium polyacryloyl dimethyl taurate, and preferably, xanthan gum, carbomer, sodium polyacrylate, an acrylate/C10-30 alkyl acrylate crosspolymer, or the like may be used.

According to an embodiment of the present invention, at least one of the first formulation and the second formulation may further comprise a neutralizer, and the neutralizer may be an acidic or alkaline material. The acidic material may be citric acid, phosphoric acid, and the alkaline material may be sodium hydroxide, ammonium hydroxide, potassium hydroxide, L-arginine, triethanolamine, tromethamine or (1,3-propanediol, 2-amino-2-(hydroxymethyl)-), and preferably, triethanolamine, arginine, or tromethamine may be used.

According to an embodiment of the present invention, the colored oil-soluble ingredient may be at least one selected from the group consisting of oil-soluble pigments, anti-inflammatory agents, anti-aging agents, UV protection agents, astringents, antioxidants, hair growth agents, hair growth agents, moisturizing agents, vitamins, amino acids, and wound healing accelerators, and may include an oil-soluble ingredient having an intrinsic color or processed to be colored. For example, guaizulene appears in blue, idebenone (hydroxydecylubiquinone) and coenzyme Q10 (ubiquinone) appear in yellow-orange, astaxanthin, ciconine and alkannin appear in red, and bisabolol appears in white, but the colors are not limited thereto and may be changed by processing.

According to an embodiment of the present invention, the oil-soluble ingredient may be at least one selected from the group consisting of: a natural product extract; an anti-inflammatory agent selected from alpha-bisabolol and guaiazulene; vitamins selected from vitamins A, D, and E; antioxidants selected from tocopherols, carotenoids, astaxanthin, alkanines, and cyconins; wound healing agents selected from retinol and retinol derivatives; and naturally-derived ingredients selected from ubiquinone and idebenone.

According to an embodiment of the present invention, the oil-soluble pigment is a natural pigment extracted from a flower, leaf, fruit or root of a plant, and specific examples of the plant from which the oil-soluble natural pigment is extracted may include nasturtium chrysanthemum, Indian mulberry extract (Neem extract), drumstick seed oil, turmeric, true coral, ivy gourd fruit, aloe vera, *Lawsonia inermis*, tulasi, basil, *Curcuma longa*, eggplant, etc.

Examples of oil-soluble red pigments include Indian mulberry leaf extract, drumstick seed oil, and nasturtium extract, examples of oil-soluble yellow pigments include turmeric extract, Indian mulberry flower extract, Indian mulberry leaf extract, true coral extract, holy basil leaf extract, and drumstick seed oil, and examples of oil-soluble blue pigments include Indian mulberry leaf extract, Indian mulberry flower extract, ivy gourd fruit extract, eggplant extract, aloe vera flower extract, jojoba seed oil, holy basil leaf extract, turmeric extract, true coral extract, etc.

The nasturtium chrysanthemum (*Eclipta prostrata*) performs hemostasis, hemolysis, calming, antibacterial action, and hair growth promoting action, and makes hair black.

The Indian mulberry tree extract (Neem, Awadirachta indiac/Melica Awadirachta) has an acne treatment effect and is used in basic cosmetic products and shampoos.

The drumstick seed oil (*Moringa pterygosperma* seed), more commonly called a Moringa tree, is a legume plant, which is a tropical tree in which the entire tree as well as leaves and fruits are edible, and contains 90 nutrients, such as a large amount of amino acids, minerals, vitamins, etc.

The turmeric (*Curcuma longa* Linne) is a perennial herb with ginger, and curcumin that is a physiologically active substance contained in turmeric, has excellent antioxidant, anti-inflammatory, and antiviral effects.

The true coral (*Corallina officinalis*) is a seaweed of the red algae coral family and is rich in calamine and minerals, which have excellent skin soothing effect.

The ivy gourd fruit (*Coccinia indica*) is used as a herbal medicine for controlling blood sugar in diabetic patients.

The aloe vera (*Barbados aloe*) has a gel-type sap contained in the leaves thereof, which is effective in treating burns and arthritis.

The jojoba oil is a wax ester of higher unsaturated alcohol and unsaturated fatty acid obtained from seeds of jojoba (*Simmondsia chinensis* or *Simmondsia califormica* Nattall), and is effective in controlling sebum by controlling sebum secretion and dissolving wastes in pores.

The *Lawsonia inermis* (scientific name) helps hair recovery and scalp health and has a treatment effect, and thus is used in hair products and is also used as red henna.

The tulasi (scientific name: *Ocimum sanctum*) is an Ayurvedic herb that is used for religious purposes or medical purposes such as antibacterial agents.

The basil (scientific name: *Ocimum basilicum*) has the effect of clearing the head and is used for ornamental, edible or flavoring purposes.

The turmeric (scientific name: *Curcuma longa*) is effective in improving liver function, and thus is widely used for medicinal purposes and is used as a yellow pigment for silk and cotton dyeing or as a food coloring agent.

The eggplant (scientific name: *Solanum melongena*) is a dicotyledonous plant of the Solanaceae family of the order *Solanum* and is mainly used for food.

The oil-soluble natural pigment of the present invention may be prepared by a method known in the art, and the method is not particularly limited. In general, a natural pigment may be prepared by separating a pigment component from an extract obtained by adding to a solvent the plant crushed after washing and drying, extracting and filtering, followed by concentrating under reduced pressure and drying.

According to an embodiment of the present invention, the second formulation may further comprise a solubilizing agent, and any solubilizing agent known in the art may be used as the solubilizing agent. For example, anionic surfactants, cationic surfactants, amphoteric surfactants, and nonionic surfactants may be used as surfactants. Specifically, the surfactant may be selected from the group consisting of castor (*Ricinus communis*) oil, ceresin, ceteareth-5, ceteareth-12, ceteareth-20, cetearyl octanoate, ceteth-20, ceteth-24, cetyl acetate, cetyl octanoate, cetyl palmitate, octyldodeceth-16, glyceryl hydroxystearate, polyglyceryl-10 laurate, polyglyceryl-10 laurate, polyglyceryl-10 linoleate, polyglyceryl-10 myristate, glyceryl oleate, glyceryl stearate, glycerol stearate SE, PEG-7 hydrogenated castor oil, PEG-40 hydrogenated castor oil, PEG-60 hydrogenated castor oil, PEG-20 methyl glucose sesquistearate, PEG-40 sorbitan ferroleate, PEG-2 stearate, PEG-8 stearate, PEG-20 stearate, PEG-32 stearate, polysorbate 20, polysorbate 40, polysorbate 60, polysorbate 80, polysorbate 85, potassium myristate, potassium palmitate, and C12-C13 pareth-12.

The solvent contained in the first formulation of the composition according to the present invention is not particularly limited, but purified water, polyols or volatile solvents, preferably purified water, 1,3-butyleneglycol, 1,3-propanediol (1,3-propandiol) or ethanol, more preferably purified water or 1,3-butylene glycol, and most preferably purified water, may be used.

The solvent contained in the second formulation is not particularly limited, but polyols are mainly used, and DPG (dipropylene glycol), preferably glycerin, 1,3-butyleneglycol, or 1,3-propandiol, more preferably 1,3-butyleneglycol or 1,3-propandiol, and most preferably 1,3-propandiol, may be used.

In the case of the first formulation, the solvent is preferably contained in an amount of 40 to 90% by weight on the basis of the total weight of the composition of the first formulation. In the case of the second formulation, the solvent is preferably contained in an amount of 60 to 95% by weight on the basis of the total weight of the composition of the second formulation.

According to an embodiment of the present invention, the cosmetic composition according to the present invention may further include various additives widely used in the art to improve storage stability and marketability of products, such as preservatives, stimulants, fragrances, pigments, antioxidants, and the like.

According to an embodiment of the present invention, the stimulant may be selected from kava kava, aloe vera gel, Machiko extract, grapefruit extract, lavender extract, willow herb extract, and the like.

According to an embodiment of the present invention, to prepare the capsules, purified water, acacia gum, and other gums other than acacia gum, and preservatives are measured and uniformly dispersed in a dissolution tank and then heated at 70-90° C., and microfluidic technology is applied to the resultant product to produce capsules containing oil-based emollients under cooling to 30-50° C. The capsules are filled with a buffer solution composed of purified water, polyol, preservatives, gums, etc. to finally prepare capsules that can be easily stored.

According to an embodiment of the present invention, in the capsule coloration cosmetic composition, a first formulation is prepared by weighing and dispersing a polyol, a thickener, a neutralizer, other additives, and an appropriate amount of a solvent, and then dispersing pre-prepared capsules. In addition, a second formulation is prepared by weighing and dispersing oil-soluble ingredients, a polyol, a solubilizer, other additives and solvents. The thus respectively prepared first and second formulations are placed into separate cases or in a fillable container that can be filled separately from the second formulation for commercial distribution, the first formulation comprising transparent capsules and the second formulation comprising an oil-soluble ingredient having a color.

A user who has purchased the capsule coloration cosmetic composition can see, before use, that the color of the capsules of the first formulation changes to the color of the second formulation by adding the second formulation to the first formulation. Accordingly, the user can identify that functional ingredients of the second formulation are included in the capsules as the functional ingredients of the second formulation are absorbed into the capsules, thereby increasing the reliability of the functionality of the cosmetic composition.

FIG. 1 is a diagram schematically showing a change in the color of capsules when an oil-soluble ingredient is absorbed into the capsules by mixing a first formulation comprising transparent capsules and a second formulation, prepared according to an embodiment of the present invention. Referring to FIG. 1, when mixing a first formulation 1 containing transparent capsules 11 and a second formulation 2 containing guaiazulene (blue) 21 as an oil-soluble ingredient), after 3 hours of the mixing, the oil-soluble ingredient 21 starts to slowly penetrate into the capsules 11, and when completely penetrating into the capsules while changing to blue, the capsules 31 containing the oil-soluble ingredient appears blue. FIG. 1 is a partially enlarged view for better illustrating the present invention, and in actually manufacturing cosmetics, capsules are much smaller and only a color change may be detected. As shown, in actual use, the user can know that the oil-soluble ingredient is completely absorbed into the capsules of the first formulation, and the change in the aesthetic appearance according to the color change may increase purchase desire. In addition, the oil-soluble ingredient, the activity of which decreases when contacting water, is excluded from contacting a large amount of water until use, and is dissolved and stabilized in the oil in the capsules even after mixing for use, thereby improving long-term stability.

Figure 2:
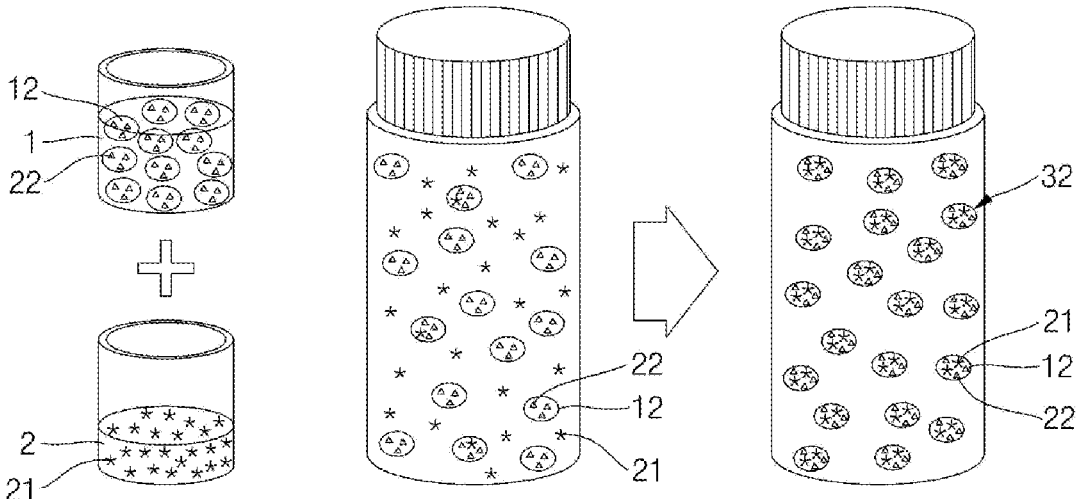
FIG. 2 is a diagram schematically showing a change in color by mixing a first formulation comprising colored capsules and a second formulation, prepared according to an embodiment of the present invention.

FIG. 2 is a diagram schematically showing a change in color by mixing a first formulation comprising colored capsules and a second formulation, prepared according to another embodiment of the present invention. Referring to FIG. 2, when the first formulation 1 containing yellow capsules 12 including oil-soluble yellow pigment 22 and the second formulation 2 containing guaiazulene 21 as an oil-soluble ingredient with a blue color are mixed, blue oil-soluble ingredient 21 slowly penetrates into the yellow capsules 12, the capsule color changes gradually, and after complete penetration, a colored cosmetic composition comprising capsules 32 containing the blue oil-soluble ingredient in the yellow capsules can be obtained.

Figure 3:
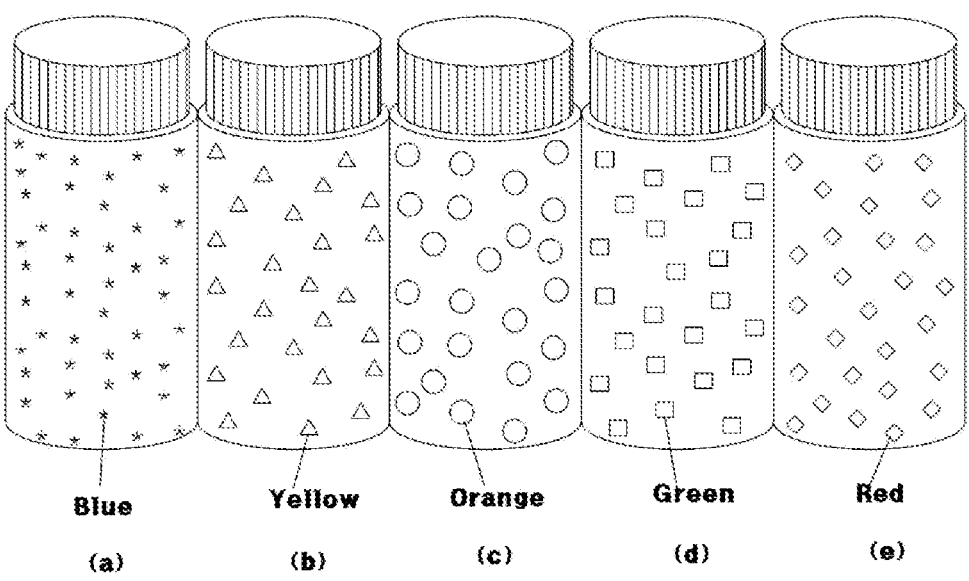
FIG. 3 is a diagram schematically illustrating a cosmetic composition in which a colored oil-soluble ingredient is absorbed into capsules and the color of the capsules is changed, according to an embodiment of the present invention.

FIG. 3 is a diagram schematically showing a capsule coloration essence cosmetic composition containing oil-soluble pigments showing respective functionalities. FIG. 3 shows the respective cosmetics according to the oil-soluble ingredient contained in capsules, for example, FIG. 3(a) schematically represents that the cosmetics can be displayed in blue, FIG. 3(b) in yellow, FIG. 3(c) in orange, FIG. 3(d) in green, and FIG. 3(e) in red, so that users can clearly identify the ingredients of each essence only by the cosmetic color, thereby providing the skin improvement effects of the cosmetics, a visually aesthetic feeling, and the effect of allowing easy selection of cosmetics even without taking a close look at the label of the cosmetics.

In addition, until the user mixes the first formulation with the second formulation, the oil-soluble ingredient can pre-vent the oil-soluble ingredient that is sensitive to water from contacting with water as much as possible, thereby increasing long-term stability.

MODE OF DISCLOSURE

Hereinafter, the present invention will be described in more detail through examples. These examples are provided only for illustrating the present invention in more detail, and it will be apparent to a person skilled in the art to which the present invention pertains that the scope of the present invention is not limited by these examples.

Experimental Example 1: Long-Term Stability Test of Oil-Soluble Ingredient

In order to determine whether the activity of the oil-soluble ingredient is changed by the change in its structure by water, by including the oil-soluble ingredient and water by stage, the degree of discoloration and change in the content of the oil-soluble ingredient were observed. After preparing the second formulation comprising the oil-soluble ingredient by mixing as shown in Table 1 below, the long-term stability of the oil-soluble ingredient was evaluated. The experimental conditions and results are indicated in Table 1 [(a) Reference Example 1, (b) Reference Comparative Example 1, (c) Reference Comparative Example 2, (d) Reference Comparative Example 3, (e) Reference Comparative Example 4]. However, the compositions of Reference Example 1 and Reference Comparative Examples 1 to 4 are provided only for evaluating the effect of water on oil-soluble ingredients, and the following formulations do not limit the scope of the second formulation of the present invention. That is, in the case of an oil-soluble ingredient that is not affected by water, the content of water may be increased.

TABLE 1

| Ingredient (Second formulation) (Unit: wt %) | | Reference Example 1 | Reference Comparative Example 1 | Reference Comparative Example 2 | Reference Comparative Example 3 | Reference Comparative Example 4 |
|---|---|---|---|---|---|---|
| Water | Purified water | — | 5 | 20 | 40 | 80 |
| Oil-soluble ingredient | Guaiazulene | 0.05 | 0.05 | 0.05 | 0.05 | 0.05 |
| [1] Polyol | (a):(b) weight ratio = 1:1 | To 100 | To 100 | To 100 | To 100 | To 100 |
| [2] Solubilizer | (c):(d) weight ratio = 1:1 | 1.0 | 1.0 | 1.0 | 1.0 | 1.0 |
| Total content | | 100 | 100 | 100 | 100 | 100 |
| Discoloration of oil-soluble ingredient | Severity stability (40° C., 4 weeks) | Visual observation | — | Slightly discolored | Slightly discolored, decolorized | Discolored, decolorized | Discolored, decolorized |
| | | RGB change | (6, 28, 116) ⇒(11, 31, 180) | (6, 28, 116) ⇒(7, 71, 144) | (6, 28, 116) ⇒(5, 63, 99) | (6, 28, 116) ⇒(5, 99, 99) | (6, 28, 116) ⇒(4, 114, 114) |
| | Daylight stability (4 weeks) | Visual observation | — | Slightly discolored | Slightly discolored, decolorized | Discolored, decolorized | Discolored, decolorized |
| | | RGB change | (6, 28, 116) ⇒(14, 66, 208) | (6, 28, 116) ⇒(5, 96, 99) | (6, 28, 116) ⇒(4, 81, 67) | (6, 28, 116) ⇒(10, 101, 85) | (6, 28, 116) ⇒(15, 126, 107) |
| | Fluorescence stability (4 weeks) | Visual observation | — | Slightly discolored | Slightly discolored, decolorized | Discolored, decolorized | Discolored, decolorized |
| | | RGB change | (6, 28, 116) ⇒(11, 56, 180) | (6, 28, 116) ⇒(5, 63, 99) | (6, 28, 116) ⇒(5, 99, 99) | (6, 28, 116) ⇒(13, 92, 94) | (6, 28, 116) ⇒(11, 124, 105) |

TABLE 1-continued

| Ingredient (Second formulation) (Unit: wt %) | | Reference Example 1 | Reference Comparative Example 1 | Reference Comparative Example 2 | Reference Comparative Example 3 | Reference Comparative Example 4 |
|---|---|---|---|---|---|---|
| Content of oil-soluble ingredient (%) | Severity stability (40° C., 8 weeks) | 97 ± 0.91 | 75 ± 0.8 | 50 ± 0.72 | 20 ± 0.91 | 15 ± 0.81 |
| | Daylight stability (8 weeks) | 95 ± 0.91 | 70 ± 0.71 | 48 ± 0.62 | 18 ± 0.84 | 13 ± 0.75 |
| | Fluorescence stability (8 weeks) | | 71 ± 0.81 | 45 ± 0.71 | 19 ± 0.82 | 12 ± 0.94 |

[1] (a) Glycerin, (b) 1,3-propanediol
[2] (c) polyglyceryl-10 laurate, (d) PEG-40 hydrogenated castor oil As can be seen from Table 1, the oil-soluble ingredient increases the extent of discoloration as the content of water increases, and it is confirmed that the content of oil-soluble ingredient decreases. That is, consequently, it can be seen that the stability of the oil-soluble ingredient decreases as the water content increases. Specifically, when the content of water exceeds 5 wt %, the stability is rapidly lowered.

Experimental Example 2: Evaluation of Absorption of Oil-Soluble Ingredient According to Capsule Outer Membrane Composition After preparing capsules with the composition shown in Table 2 below, a first formulation was prepared in the following manner, and a second formulation comprising blue guaiazulene as an oil-soluble ingredient was then prepared, followed by mixing the first formulation and the second formulation. After 6 hours at room temperature, changes were observed. The results are shown in Table 2 and FIG. 4. The weight percentages of the first and second formulations below are based on 100 wt % of the total content of the first and second formulations.

cooling to 4° C. The capsules were filled with a buffer solution composed of purified water, polyol, preservative, gum, etc. to finally prepare capsules that can be easily stored.

Preparation of First Formulation

The first formulation was prepared by mixing 5 wt % of the prepared capsules, 0.1 wt % of tromethamine as a neutralizer, 0.2 wt % of carbomer as a thickener, 10 wt % of glycerin as a polyol, and 74.7 wt % of water.

Preparation of Second Formulation

The second formulation was prepared by mixing 0.01 wt % of guaiazulene, 0.5 wt % of PEG-40 hydrogenated castor oil, and 9.49 wt % of glycerin.

Preparation of Capsule Coloration Cosmetic Composition

The prepared first and second formulations were mixed in a weight ratio of 1:0.1. After mixing, it was confirmed that the oil-soluble ingredient of the second formulation was incorporated into the capsules of the first formulation, and the results were confirmed in Table 2 (observed after 6 hours) and FIG. 4 (observed after 3 days), respectively.

TABLE 2

| | | | | | |
|---|---|---|---|---|---|
| | | | (Unit:wt %) | | |
| Ingredient | Example 1 | Example 2 | Comparative Example 1 | Comparative Example 2 | Comparative Example 3 |
| Water | To 100 | To 100 | To 100 | To 100 | To 100 |
| Acacia Senegal gum | 3 | 3 | 3 | — | — |
| Gelatin | 2 | — | — | 2 | — |
| Aribic Gum | — | — | — | — | 3 |
| Hydrolyzed collagen | — | — | — | — | — |
| Cellulose gum | — | — | — | 3 | — |
| Agar | — | 2 | — | — | 2 |
| Gellan gum | — | — | 2 | — | 0.3 |
| Dimethicone:squalene weight ratio = 1:1 | 82.0 | 82.0 | 82.0 | 82.0 | 82.0 |
| Glycerin | 2.0 | 2.0 | 2.0 | 2.0 | 2.0 |
| Confirmation of capsule penetration (after 6 hours) | Oil-soluble ingredient moved into capsules | Oil-soluble ingredient moved into capsules | Not moved | Not moved | Not moved |

Preparation of Capsules

Figure 4:
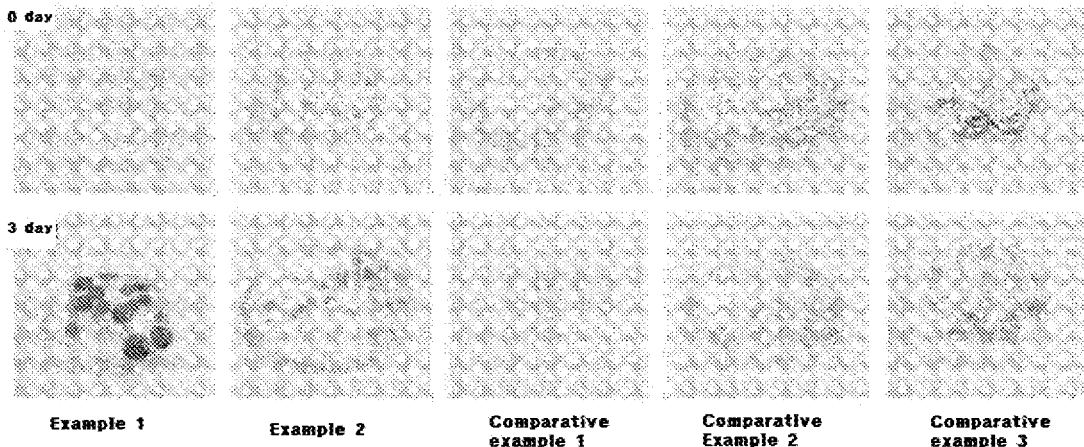
FIG. 4 is a photograph showing the absorption rate of the oil-soluble ingredient according to the composition of an outer membrane of capsule according to Experimental Example 2.

The capsules were measured with the composition of Table 2, purified water, acacia gum, other gums other than acacia gum, and preservatives were measured and uniformly dispersed in a dissolution tank, heated at 8° C. for 1 hour, and microfluidic technology was then applied thereto to prepare the capsules containing oil-based emollients under As can be seen from Table 2 and FIG. 4, it is confirmed that in the case of the formulation including the capsules containing the acacia gum prepared according to the present invention, the penetration of the oil-soluble ingredient is easy for the same time. Specifically, referring to Table 2 and FIG. 4, according to the present invention, in Examples 1 and 2 in which acacia gum and gelatin, and acacia gum and agar are included, respectively, the oil-soluble ingredients were completely absorbed into capsules. However, in Comparative Example 1 in which only acacia gum is included, or in Comparative Examples 2 and 3 in which gelatin or agar is included but acacia gum is not included, the oil-soluble ingredient was not induced into the prepared capsules but existed outside the capsules. In addition, as shown in FIG. 4, even after 3 days have elapsed, the capsules into which the oil-soluble ingredient has been absorbed were maintained without changing the appearance thereof, thereby confirming the long-term stability of the capsules containing the oil-soluble ingredient.

Therefore, only by the capsule coloration cosmetic composition according to the present invention, a change in color and an inflow of oil-soluble ingredient into the capsules, can be achieved, thereby enhancing the long-term stability of the oil-soluble ingredient as well as aesthetics.

Figure 5:
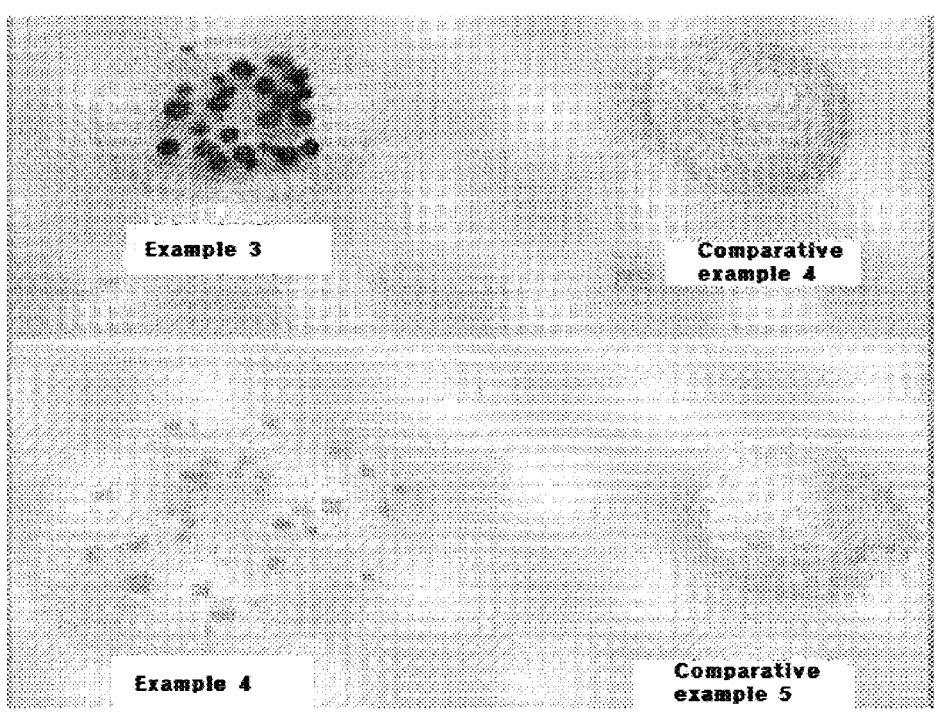
FIG. 5 shows photographs illustrating the inflow of an oil-soluble ingredient into an oil-based emollient inside capsules and outer membranes of capsule according to Experimental Example 3.

Experimental Example 3: Confirmation of Inflow of Oil-Soluble Ingredient into Oil-Based Emollient Inside Capsules In order to confirm that the discoloration of capsules was caused by the inflow to the oil-based emollient inside the capsules, not by the discoloration of the outer membranes of the capsules, but was induced, capsules were prepared with the composition shown in Table 3 below. With regard to cosmetic compositions, the same procedure was performed as in Example 1, except for the preparation method of capsules, and the results thereof are indicated in Table 3 and FIG. 5.

TABLE 3

| | | | (Unit:wt %) | |
| --- | --- | --- | --- | --- |
| Ingredient | Example 3 | Example 4 | Comparative Example 4 | Comparative Example 5 |
| Purified water | To 100 | To 100 | To 100 | To 100 |
| Acacia Senegal gum | 3 | 3 | 3 | 3 |
| Gelatin | 2 | — | 2 | — |
| Agar | — | 2 | — | 2 |
| Dimethicone:squalene weight ratio = 1:1 | 82.0 | 82 | — | — |
| Moisturizer | 3 | 3 | 3 | 3 |
| Result (after 2 weeks) | Movement of oil-soluble ingredient into capsules, confirmed | Movement of oil-soluble ingredient into capsules, confirmed | Not moved into capsules | Not moved into capsules |

As can be seen from Tables 3 and 5, in Comparative Examples 4 and 5 in which no oil existed in the capsules, discoloration was not observed. This suggests that the oil-soluble ingredient did not exist on the outer membranes of the capsules but penetrated into the outer membranes and existed in oil-based emollients. Therefore, the cosmetic composition according to the present invention is stored in the oily layer even after mixing the first formulation and the second formulation immediately before use, thereby increasing long-term stability.

Experimental Example 4: Preparation of Capsules According to Changes in Mixed Gum Content Capsules were prepared with the composition shown in Table 4 below according to the method described in Example 1.

A case in which more than 95% of all of the capsules maintains an intact shape is referred to as being "good", a case in which 80 to 95% of capsules maintains an intact shape is referred to as being "normal", and a case in which 80% or less of capsules maintains an intact shape is referred to as being "partly modified".

TABLE 4

| | (Unit:wt %) | | | |
| --- | --- | --- | --- | --- |
| Ingredient | Example 5 | Example 6 | Example 7 | Example 8 |
| Water | To 100 | To 100 | To 100 | To 100 |
| Mixed gum of Acacia Senegal gum and gelatin in weight ratio of 1:0.5 | 3 | 7 | 1 | 10 |
| Dimethicone:squalene weight ratio = 1:1 | 82.0 | 82.0 | 82.0 | 82.0 |
| Glycerin | 2.0 | 2.0 | 2.0 | 2.0 |
| Capsule state | Good | Good | Thin capsules formed | Thick capsules formed |
| Capsule shape retention (after 6 months) | Good | Good | Partly modified | Partly modified |

As can be seen from Table 4, when capsules are prepared with a mixed gum containing acacia gum, the capsule coloration cosmetic composition according to the present invention may be prepared by forming the capsules. However, if the capsules are not included in the preferred range, some of the capsules may be modified in shape during long-term storage. Accordingly, it is more preferable for the capsules to be included in a preferred range in terms of long-term stability.

Experimental Example 5: Evaluation of Long-Term Shape Retention of Capsules According to Content of Acacia Gum Capsules were prepared with the composition shown in Table 5 below, and the long-term shape retention of the capsules was evaluated. The capsule coloration cosmetic composition was prepared in the same manner as in Example 1, except for the amount of the mixed gum, and the evaluation method is the same as that of Experimental Example 4.

TABLE 5

| | (Unit:wt %) | | | |
| --- | --- | --- | --- | --- |
| Ingredient | Example 9 | Example 10 | Example 11 | Example 12 |
| Acacia Senegal gum | 5 | 0.5 | 6 | 2 |

TABLE 5-continued

| | | | (Unit:wt %) | |
|---|---|---|---|---|
| Ingredient | Example 9 | Example 10 | Example 11 | Example 12 |
| Capsule shape retention (after 6 months) | Good | Normal | Normal | Good |

As can be seen from Table 5, when capsules are prepared by including acacia gum beyond a preferred range, it may be difficult to maintain the shape of the capsules for a long period of time. Therefore, for long-term stability, it is preferable to prepare the capsules so as to include the acacia gum in a preferred range.

Experimental Example 6: Evaluation of Oil-Soluble Ingredient Potency Retention According to Encapsulation In order to examine the effect of the encapsulation used in the present invention on maintaining the potency of the oil-soluble ingredient, the amount of guaiazulene was measured using HPLC.

An encapsulated cosmetic composition was prepared with the composition of Example 3 and Comparative Example 4. The composition was stored at 25° C. while blocking light and air, and analyzed using HPLC (Promience 20 set, Dongil Shimadzu, JAPAN) on day 3 and one month, and the results are shown in Table 6 below.

TABLE 6

| Guaiazulene content analysis result (Unit:wt %) | | |
|---|---|---|
| | Example 3 | Comparative Example 4 |
| Day 3 | 0.00093 | 0.00088 |
| One month | 0.00090 | 0.00075 |

As can be seen from Table 6, in Example 3 in which guaiazulene as an oil-soluble effective ingredient, was encapsulated, it was confirmed that the potency retention was about 20% higher than that of Comparative Example 4 in which the encapsulation was not performed.

The invention claimed is:

1. A capsule coloration cosmetic composition comprising:
a first formulation comprising capsules; and
a second formulation comprising a colored oil-soluble ingredient, the second formulation being water-free, wherein the first formulation and the second formulation are included in a weight ratio of 1:0.01 to 1:0.3;
wherein outer membranes of the capsules in the first formulation comprise a mixed gum comprising:
acacia senegal gum; and
at least one of gelatin and agar,
wherein an oil-based emollient is included inside the capsules;
wherein the mixed gum is included in an amount of 1 to 10 wt %, based on a total weight of the capsules;
wherein in the mixed gum, the acacia senegal gum and other gums including the at least one of gelatin and agar are mixed in a weight ratio of 1:0.01 to 1:1;
wherein the oil-based emollient is included in an amount of 50 to 85 wt %, based on the total weight of the capsules in the first formulation;
wherein the oil-based emollient comprises any two or more selected from the group consisting of ethylhexystearate, isopropyl myristate, ethyl laurate, ethyl myristate, isopropyl palmitate, triglyceride, diglyceride, monoglyceride, glyceryl trioctanoate, octadodecyl myristate, isostearyl isostearate, dicapryl carbonate, octyl palmitate, caprylic/capric triglyceride, butylene glycol dicaprylate/dicaprate, triethylhexa senile, cetylethylhexanoate, octyldodecanol, liquid paraffin, petrolatum, hydrogenated polydecene, squalene, cyclomethicone, phenyltrimethicone, cyclopentasiloxane, and dimethicone;
wherein the colored oil-soluble ingredient is included in an amount of 0.001 to 5 wt %, based on a total weight of the second formulation;
wherein water is included in an amount of less than 10 wt % in the capsules based on the total weight of the capsules in the first formulation; and
wherein the oil-soluble ingredient is included in the second formulation without water while being separated from the first formulation.

2. The capsule coloration cosmetic composition of claim 1, wherein the capsules are included in an amount of 0.01 to 50 wt %, based on the total weight of the first formulation.

3. The capsule coloration cosmetic composition of claim 1, wherein the first formulation further includes a polyol, and the capsules and the polyol are mixed in a weight ratio of 1:1 to 1:3.

4. The capsule coloration cosmetic composition of claim 1, wherein the colored oil-soluble ingredient has an intrinsic color or is processed to be colored.

5. The capsule coloration cosmetic composition of claim 1, wherein water is not included inside the capsules.

* * * * *